United States Patent [19]
Chang

[11] Patent Number: 6,022,327
[45] Date of Patent: Feb. 8, 2000

[54] FACIAL STEAMER MACHINE WITH DETACHABLE FUNCTION UNITS

[76] Inventor: Henry Ping Chang, 2345 Ridgeway Rd., San Marino, Calif. 91108

[21] Appl. No.: 09/072,575

[22] Filed: May 4, 1998

[51] Int. Cl.[7] .............................. A61H 7/00; H05K 7/14
[52] U.S. Cl. ........................... 601/15; 601/16; 601/138; 361/727; 248/129; 211/131.1; 312/223.1; 312/249.8
[58] Field of Search .................................. 361/724, 725, 361/726, 727, 730–3; 248/128, 129; 211/70.6, 133.1; 312/209, 223.1, 249.8; 433/77–79; 601/7, 15, 16, 17, 46, 84, 137, 138

[56] References Cited

U.S. PATENT DOCUMENTS

| | | |
|---|---|---|
| 2,691,724 | 10/1954 | Hoffman . |
| 4,236,190 | 11/1980 | Hollingsead et al. . |
| 4,882,655 | 11/1989 | Pavie . |
| 4,939,622 | 7/1990 | Weiss et al. . |
| 5,211,558 | 5/1993 | Bailey et al. . |
| 5,793,614 | 8/1998 | Tollbom . |

*Primary Examiner*—Danton D. DeMille
*Attorney, Agent, or Firm*—Raymond Chan; David and Raymond

[57] ABSTRACT

The present invention provides a facial steamer machine with detachable function units, in which all kinds of skin care appliance are independently constructed into a plurality of function units which are adapted to incorporate with the facial steamer machine, so that the user may selectively combine several function units to detachably connect and equip with the facial steamer machine to form a single skin care system. The facial steamer machine of the present invention can also reduce the overall manufacturing cost by utilizing some common components such as the movable stand and the power wiring arrangement. Therefore, the present invention occupies less storage space and operating space. Moreover, it is easier to maintain too.

26 Claims, 6 Drawing Sheets

FACIAL STEAMER MACHINE WITH DETACHABLE FUNCTION UNITS

FIELD OF THE INVENTION

The present invention relates to a facial steamer machine, and more particularly to a facial steamer machine with detachable function units, in which the facial steamer machine is adapted to selectively incorporate with various skin care function units to form a single system, in order to achieve the advantages of lower basic cost, less storage space and easier maintenance.

BACKGROUND OF THE INVENTION

Nowadays, people generally judge another by how he or she looks because it is the first resource that people present themselves to others. Therefore, in order to look younger and healthier, it is getting more and more popular for people spending time to have skin care in beauty shops to protect their skins and to clean their faces by the cosmeticians or estheticians.

There are plenty of standard tools that the cosmetician or esthetician needs to utilize during facial cleaning or other types of facial work. These tools include the facial steamer machine which can generate warm water steam to provide treatment of softening the skin, opening pores, and improving skin respiration, the vacuum-spray which can provide vacuum suction for deep cleaning and plumping out wrinkles with spray for liquid cosmetics and toning application, the electrical brush for deep cleaning treatment, the hot and cold treatment appliance for skin pores expansion and contraction, and the lymphatic drainage treatment appliance such as the rhythmic air massage, vacuum massage or air patting massage that can create a deep kneading, wave like action, or perform gliding and pulsing. Other more advancing tools include the high frequency current device for providing stimulating and a germicidal action, the galvanic current device for ionization and desincrustation treatment, the hair removal apparatus for depletion of hair, the ultrasound device for massaging the skin, and the faradic current device for muscle toning or muscle exercising.

In view of above, there are so many different types of skin care appliance, however most of the conventional beauty care appliances are designed to merely accomplish a single function. In other words, the function of each beauty care appliance is limited and the user must spend more expense to purchase so many kinds of skin care appliance. Each skin care appliance must be built to form a single machine that has an individual supporting stand and an extended electrical wire for power supply. Therefore, they need more space to store and various machines with different purposes are require to arrange around the patient's treatment bed at the same time for each facial treatment that occupies a lot of space and complicates the application of each machine. Moreover, since each machine has an independent power wire, it is very troublesome and dangerous for the cosmetician or esthetician to handle so many wiring around the patient.

Recently, some manufacture combines two to three types of appliance into one machine, that provides more functions in a single machine, takes up less space, and also becomes more economic in cost. However, the combination machine still has its shortcomings, such as: 1) the functions of each multi-purpose machine are still limited, so that the cosmetician might still have to purchase more than one combination machine; 2) different types of appliance are not replaceable, so that different multi-purpose machines might poss appliances with the same function; 3) some of the functions are not used often enough, so that existence of such appliance that performs such particular function is not practical; and 4) all machines are due to have mechanical problems, that when problems occur on one of the appliances, the user needs to sent the whole multi-purpose machine back to the manufacturer to repair, therefore not only the regular work routine of the user is disturbed during the repairing time, but also that the multi-purpose machine may be further damaged during the transportation.

SUMMARY OF THE INVENTION

The main objective of the present invention is to provide a facial steamer machine with detachable function units, in which all kinds of skin care appliance are independently constructed into a plurality of function units which are adapted to incorporate with the facial steamer machine, so that the user may selectively combine several function units to detachably connect and equip with the facial steamer machine to form a single skin care system.

Another objective of the present invention is to provide a facial steamer machine with detachable function units, which can reduce the overall manufacturing cost by utilizing some common components such as the movable stand and the power wiring arrangement. Therefore, the present invention occupies less storage space and operating space. Moreover, it is easier to maintain too.

Another objective of the present invention is to provide a facial steamer machine with detachable function units, wherein predetermined function units which have different skin care functions can be replaced and arranged customly to combine with the facial steamer machine according to the substantial need of the work that the cosmetician has to perform for different individual case.

Another objective of the present invention is to provide a facial steamer machine with detachable function units, wherein a central power control is provided for all the function units equipped with the facial steamer machine.

Another objective of the present invention is to provide a facial steamer machine with detachable function units, wherein each function unit can be repaired independently during malfunction, so that other normal functioning function units can still perform regular routine without getting affected. Even if one of the detachable function units is unable to be fixed, the user may merely replace that damaged function unit with a new one.

In order to accomplish the above objectives, the present invention provides a facial steamer machine equipped with a plurality of detachable function units each having a specific skin care function. The facial steamer machine comprises a facial steamer unit, a system housing and a movable stand for supporting the facial steamer unit and the system housing. The system housing comprises a central power control unit affixed to a side of the facial steamer unit and a unit holding shelf integrally mounted on the central power control unit. The unit holding shelf provides a plurality of receiving chambers to receive the plurality of function units respectively. The central power control unit comprises a plurality of power source terminals, wherein each of the power source terminals is respectively mounted on a rear wall of each of the receiving chambers of the unit holding shelf and electrically connected to a main power wire of the facial steamer machine which is downwardly extended outside from a bottom portion of the movable stand. Each of the function units comprises a unit case to encase a specific skin care appliance therein, an operation panel provided on the unit case, a tool connector for electrically connected with an operation tool through an extensible electric wire, and a power connecting terminal disposed on a rear side of the unit case.

Therefore, when the function unit is firmly installed to facial steamer machine by inserting into the respective receiving chamber of the unit holding shelf, the power connecting terminal can be fitly connected with the respective power source terminal to achieve electrical communication. In other words, the electrical power of each function unit installed to the facial steamer machine is provided from the power source terminal through the power connecting terminal.

The user may simply detach a particular function unit from the facial steamer machine by pulling out the function unit form the receiving chamber of the unit holding shelf and disconnecting the power source terminal and the power connecting terminal. Accordingly, the user of the present invention can only purchase and store a number of relatively small sized function units and select several predetermined function units to equip with the facial steamer machine. Besides, the user can replace any function unit with another easily.

DETAILED DESCRIPTION OF THE PREFERRED EMBODIMENTS

Figure 1:
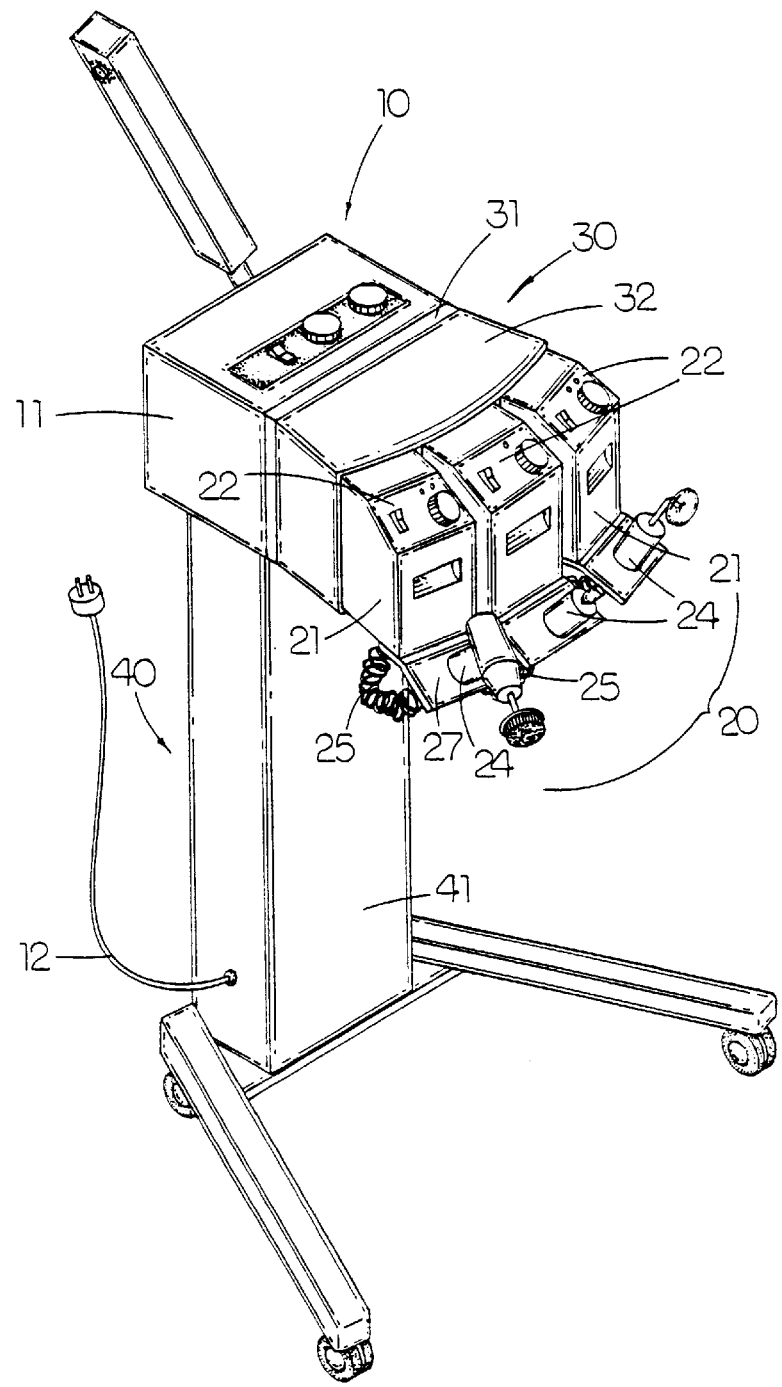
FIG. 1 is a perspective view of a facial steamer machine with detachable function units according to a first preferred embodiment of the present invention.

Referring to FIGS. 1 to 4, a first preferred embodiment of the present invention provides a facial steamer machine equipped with a plurality of detachable function units 20 each having a specific skin care function. The facial steamer machine 10 comprises a facial steamer unit 11, a system housing 30 and a movable stand 40 for supporting the facial steamer unit 11 and the system housing 30.

Each of the function units 20 comprises a unit case 21 to encase a specific skin care appliance therein, an operation panel 22 provided on the unit case 21 for controlling the operation of the specific skin care appliance, a tool connector 23 preferably provided at a front edge of a bottom side of the unit case for electrically connected with an operation tool 24 through an extensible electric wire 25, and a power connecting terminal 26 disposed on a rear side 211 of the unit case 21. A tool holder 27 is mounted on each of the unit cases for holding the operation tool 24 while it is not in use.

The skin care appliances encased in the function units should be different with each other, such as the vacuum-spray, the electrical brush, the hot and cold treatment appliance, the lymphatic drainage treatment appliance such as the rhythmic air massage, vacuum massage, and air patting massage, the high frequency current device, the galvanic current device, the hair removal apparatus, the ultrasound device, the faradic current device, and etc.

Figure 3:
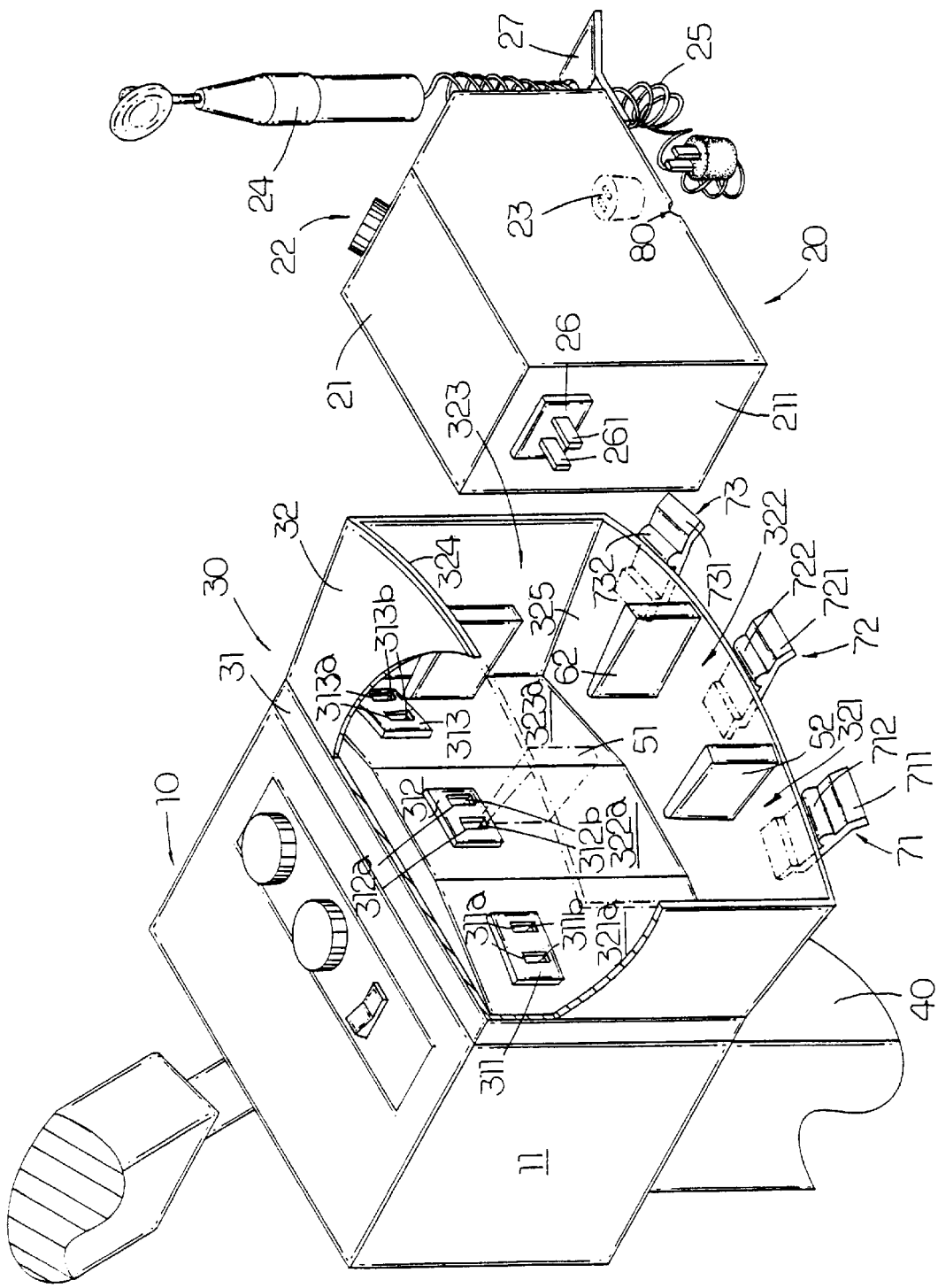
FIG. 3 is an exploded partial and sectional perspective view illustrating the unit holding shelf and one of the function units according to the above first preferred embodiment of the present invention.

According to the first embodiment of the present invention, as shown in FIG. 3, the power connecting terminal 26 is an electrical plug serving as a power input of the skin care appliance encased inside the unit case 21. Each of the electrical plugs 26 is firmly affixed to the rear side 211 of the respective unit case 21 and comprises two connecting tails 261 protruding rearwardly from the rear side 211. Certainly, any other types of electrical connector can be used to substitute the electrical plug embodied in the present invention.

Figure 4:
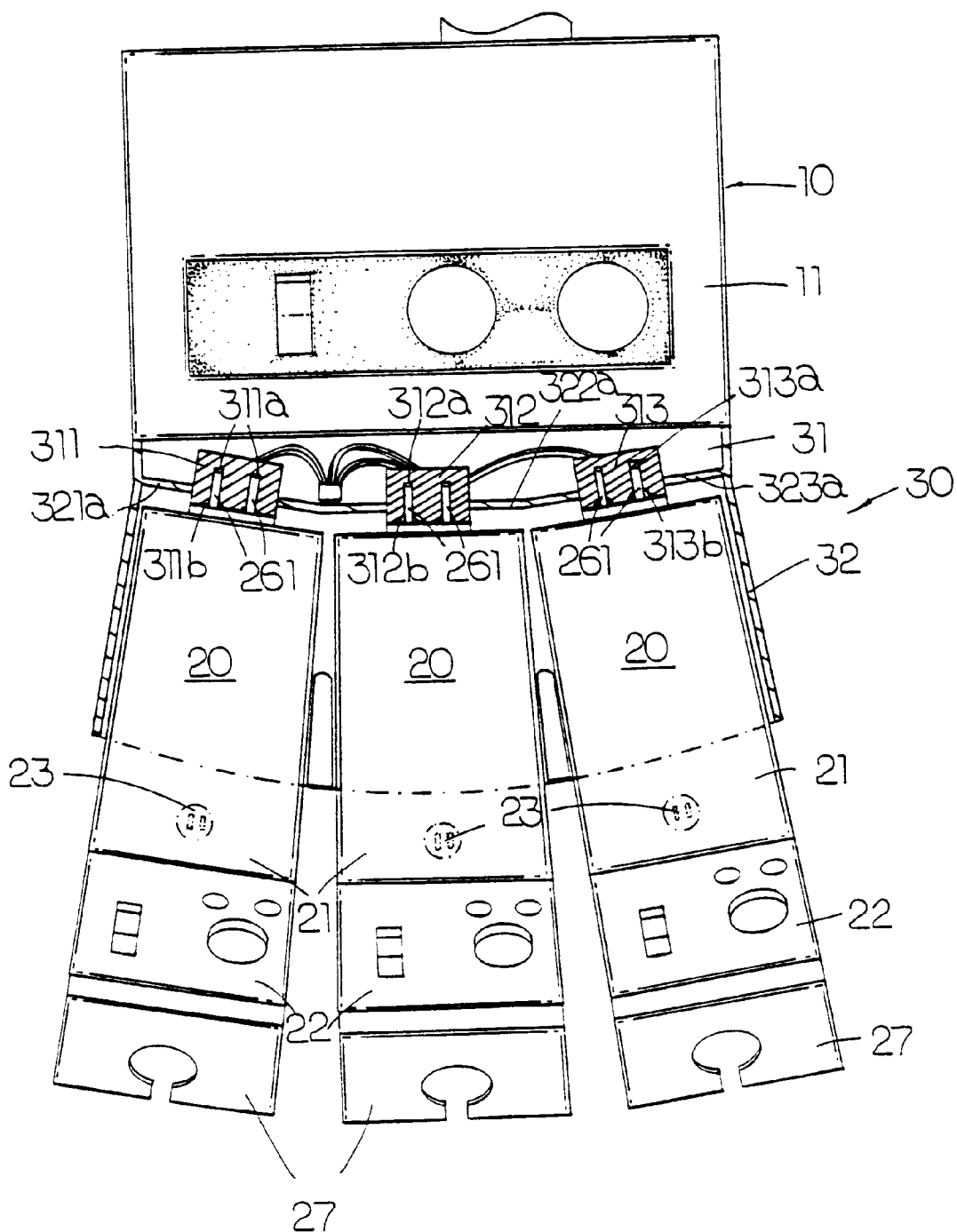
FIG. 4 is a partial sectional top view of the facial steamer machine with detachable function units according to the above first preferred embodiment of the present invention.

The system housing 30 comprises a central power control unit 31 affixed to a side of the facial steamer unit 11 and a unit holding shelf 32 integrally mounted on the central power control unit 31. As shown in FIGS. 3 and 4, the unit holding shelf 32 provides a plurality of receiving chambers 321, 322, 323 adapted to receive the plurality of function units 20 respectively. According to the present embodiment, there are three receiving chambers and three function units adapted to be held in position by partially sliding into the three receiving chambers respectively.

Figure 2:
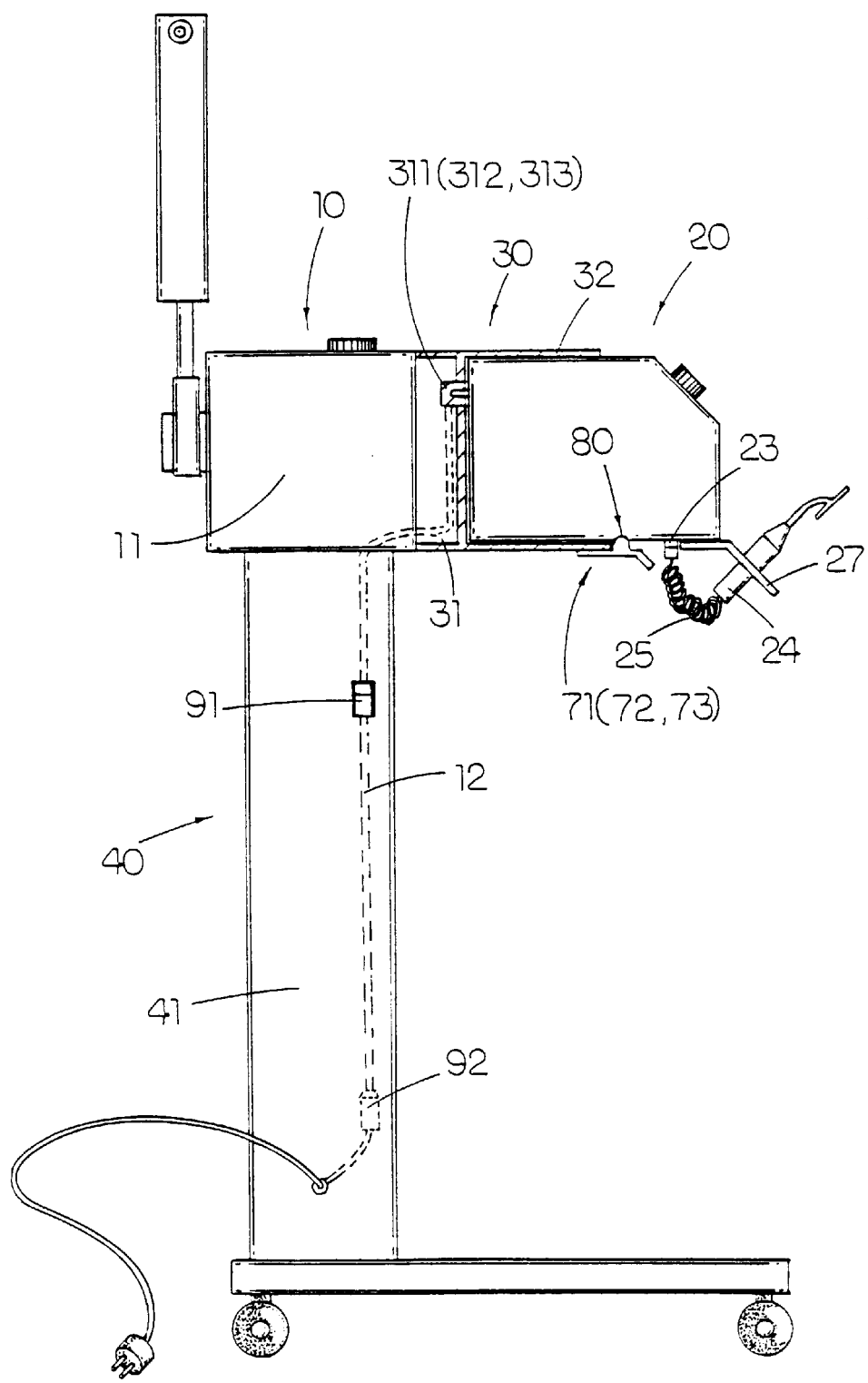
FIG. 2 is a end view of the facial steamer machine with detachable function units according to the above first preferred embodiment of the present invention.

The central power control unit 31 comprises a plurality of power source terminals 311, 312, 313, wherein each of the power source terminals 311, 312, 313 is respectively mounted on a rear wall 321a, 322a, 323a of each of the receiving chambers 321, 322, 323 of the unit holding shelf 32 (as shown in FIG. 3) and electrically connected to a main power wire 12 of the facial steamer machine 10 (as shown in FIGS. 1 and 2) which is downwardly extended outside from a bottom portion of a supporting stem 41 the movable stand 40.

In order to facilitate the user to operate the three function units 20, the three function units 20 are preferably arranged angularly, so that the two sideward positioned rear walls 311, 313 of the unit holding shelf 32 are rearwardly inclined with respect to the middle rear wall 312. As shown in FIG. 3, two pairs of dividers 51, 52, 61, 62 are secured to a top wall 324 and a bottom wall 325 of the unit holding shelf 32 respectively, wherein each of the dividers 51, 52, 61, 62 comprises a tapered wedge. Two of the dividers 51, 61 are evenly spaced and parallelly secured to the top wall 324 while the other two dividers 52, 62 are evenly spaced and parallelly secured to the bottom wall 325 so as to define the three receiving chambers 321, 322, 323 therebetween.

According to the present embodiment, each of the power source terminals 311, 312, 313 is an electrical socket which has two parallel socket holes 311a, 312a, 313a and serves as a power output of the facial steamer machine 10, wherein a front surface of each electrical socket 311, 312, 313 is preferably positioned at the same plane of the respective rear wall 321a, 322a, 323a, so that when the respective function unit 20 is inserted into the receiving chamber 321, 322, 323, the rear side 211 of the unit case 21 can be in the proximity of the corresponding rear wall 321a, 322a, 323a in order to achieve better electrical connection between the electrical plug 26 and the electrical socket 311, 312, 313. Certainly, other electrical connector can also substitute such electrical socket 311, 312, 313.

Therefore, as shown in FIGS. 3 and 4, when the function units 20 are firmly installed to the facial steamer machine 10 by inserting into the receiving chambers 321, 322, 323 of the unit holding shelf 32 respectively, the three electrical plugs 26 are fittedly connected with the electrical sockets 311, 312, 313 respectively by inserting the two connecting tails 261 of each electrical plug 26 into the two socket holes 311a, 312a, 313a of each electrical socket 311, 312, 313 to achieve electrical communication. In other words, the electrical power of each function unit 20 installed to the facial steamer machine 10 is provided from the electrical socket (power output) 311, 312, 313 through the electrical plug (power input) 26.

Moreover, the front end of each of the socket holes 311a, 312a, 313a is enlarged to front a guiding end 311b, 312b, 313b to guide the insertion of the respective connecting tail 261 of the corresponding plug 26.

For ensuring the connection between the facial steamer machine 10 and the function units 26, a plurality of locking means 71, 72, 73 are provided for respectively securing the function units 26 with the unit holding shelf 32. As shown in FIGS. 2 and 3, each of the locking means 71, 72, 73 includes a transverse groove 80 provided at a bottom surface of the unit case 21 of each function unit 20 and a resilient locking member 711, 721, 731 affixed underneath the bottom wall 322 of the unit holding shelf 32. Each of the locking member 711, 721, 731 has a securing rib 712, 722, 732 protruded upwardly for engaging with the groove 80 when the respective function unit 20 is fully inserted into the corresponding receiving chamber 321, 322, 323, as shown in FIG. 2. To unlock the locking means 71, 72, 73, the user may simply press the locking member 711, 721, 731 downwards, and then the user may detach the function unit 20 by pulling out the function unit 20 from the unit holding shelf 32. Practically, the pulling out action will plug out the electrical plug 26 from the electrical socket 311, 312, 313 simultaneously.

As shown in FIG. 2, the facial steamer machine 10 of the present invention further comprises a central switch 91, which is electrically connected along the main power wire 12. The central switch 91 can be disposed on the supporting stem 41 of the movable stand 40 so that the user may simply switch off the central switch 91 that can shut off the facial steamer unit 11 and all the function units 20 at the same time. A fuse 92 is preferably electrically connected along the main power wire 12 to protect the whole system from unwanted and unexpected electrical shock.

Figure 5:
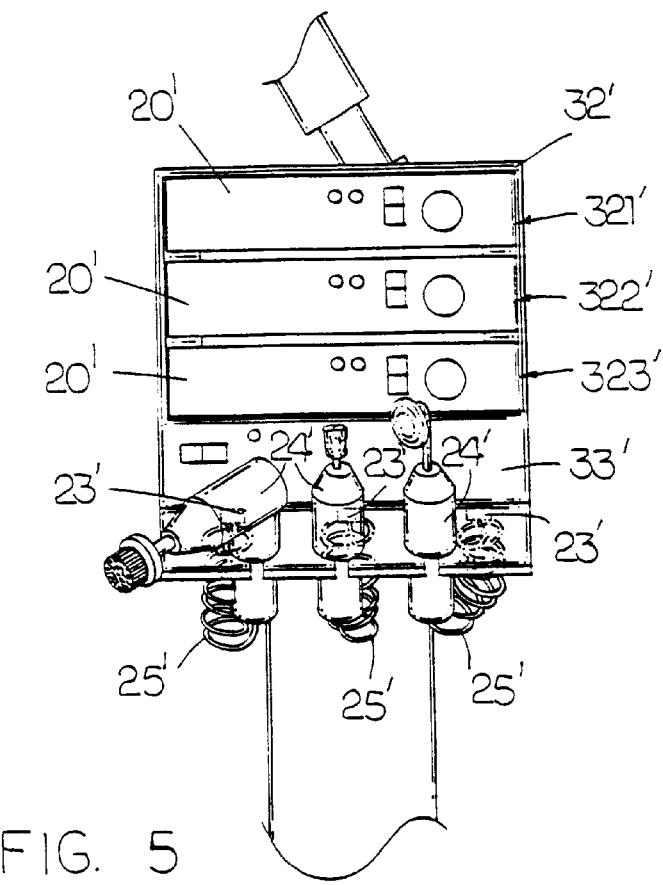
FIG. 5 is a front view of a facial steamer machine with detachable function units according to a second preferred embodiment of the present invention.
Figure 6:
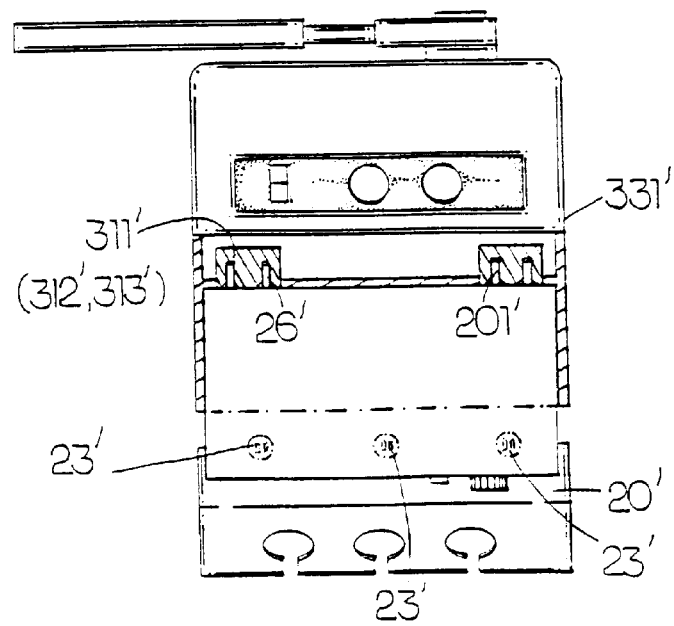
FIG. 6 is a top view of the facial steamer machine with detachable function units according to the above second preferred embodiment of the present invention.
Figure 7:
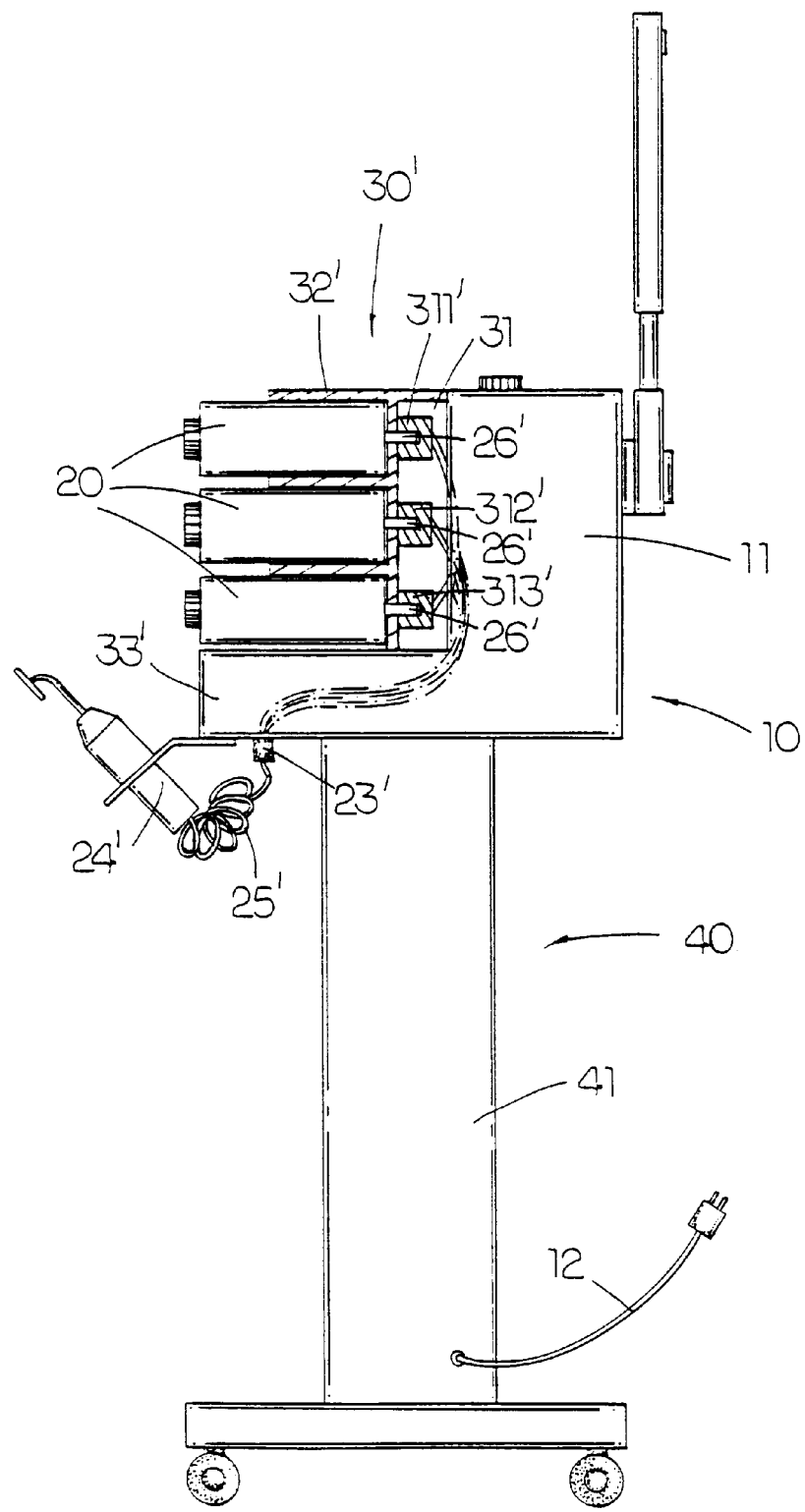
FIG. 7 is a side view of the facial steamer machine with detachable function units according to the above second preferred embodiment of the present invention.

Referring to FIGS. 5 to 7, a second preferred embodiment of the present invention is illustrated, wherein the facial steamer machine 10 is similar to the above first embodiment except the function units 20' are alternatively arranged horizontally. The facial steamer machine 10 also comprises a facial steamer unit 11, a system housing 30' and a movable stand 40. The system housing 30' also includes a central power control unit 31 affixed to a side of the facial steamer unit 11 and a unit holding shelf 32'. The unit holding shelf 32' comprises a plurality of horizontal receiving chambers 321', 322', 323' adapted to receive a plurality of function units 20' respectively. The central power control unit 31 contains a plurality of power source terminals 311', 312', 313' such as electrical sockets which are respectively mounted on the rear walls of the receiving chambers 321', 321', 331'. Each function unit 20' basically has the same structure as in the above first embodiment but in shape of rectangular, wherein each function unit 20' also comprises a power connecting terminal 26' such as an electrical plug, as shown in FIG. 7, which would be fittedly connected with the respectively power source terminal 311', 312', 313' when the functional unit 20' is fully inserted into the corresponding receiving chamber 321', 322', 323' of the unit holding shelf 32' for electrical communication with power supply (i.e. the main power wire 12) of the facial steamer machine 10.

In order to avoid the confusion of the electric wires 25' of the function units 20' and for better organizing the operation tools 24' and the electric wires 25', the facial steamer machine 10 of the second embodiment further comprises an operation unit 33' which is affixed under the unit holding shelf 32' and comprises a plurality of electrical connectors 331' all electrically extended to the rear walls of the receiving chambers 321', 322', 323' respectively. Each function unit 20' also further provides an electrical terminal 201' at the rear side thereof for electrically connected with the respectively electrical connector 331' when the function unit 20' is received in the corresponding receiving chamber 321', 322', 323', as shown in FIG. 6. The operation unit 33', in addition, provides a plurality of tool connectors 23' thereon to connect with the operation tools 24' via the electric wires 25' respectively.

In view of the above disclosure, the facial steamer machine with detachable function units of the present invention can apparently achieve the following advantages:

Flexibility: The cosmetician can select several kinds of skin care appliance to equip with the facial steamer machine for each therapy session. In other words, the user may custom make the whole system to fit the needs. Also, according to the innovative design of the plug and socket connection, the electrical plug provided on the rear side of each detachable function unit can be easily plugged into or out from a respective electrical socket of the receiving chamber during exchanging and replacing process.

Cost Efficiency: The cosmetician can purchase the individual function unit alone without buying some unused components.

Easy Maintenance and Repairing: It is because each detachable function unit is independently run, when one is broken, the normal routine of the other function units of the entire system would not be affected. The user can simply send in the broken unit to the manufacturer for replacement or repairing. Conventionally, the user has to send the whole machine to the manufacturer for merely repairing a single malfunctioning problem.

Less Storage Space: The present invention combines different appliances with different functions into one single machine, so that the space required to store is relative less than before. For those unused function units, the compact size of each function unit enable the user to store those function units in a relatively small area. Moreover, during operation, the user will not suffer in operating several large machines around the patient.

Easy to Operate: The present invention has a central power control unit provided for all appliances, therefore, the user can switch off the whole system, including the facial steamer unit and all function units simultaneously.

What is claimed is:

1. A facial steamer machine equipped with a plurality of detachable function units each having a predetermined skin care function, wherein said facial steamer machine comprises a facial steamer unit, a system housing, and a movable stand for supporting said facial steamer unit and said system housing, said system housing comprising a central power control unit affixed to a side of said facial steamer unit and a unit holding shelf integrally mounted on said central power control unit, said unit holding shelf providing a plurality of receiving chambers adapted to receive said plurality of function units respectively, said central power control unit comprising a plurality of power source terminals, wherein each of said power source terminals is respectively mounted on a rear wall of each of said receiving chambers of said unit holding shelf and electrically connected to a main power wire of said facial steamer machine which is downwardly extended outside from a bottom portion of said movable stand, each of said function units further comprising a unit case to encase a predetermined skin care appliance therein, an operation panel provided on said unit case, a tool connector provided on said unit case for electrically connected with an operation tool through an extensible electric wire, and a power connecting terminal disposed on a rear side of said unit case, therefore when said function unit is firmly installed to said facial steamer machine by inserting into said respective receiving chamber of said unit holding shelf, said power connecting terminal is fittedly connected with said respective power source terminal in order to achieve electrical communication, so that an electrical power of each of said function units installed to said facial steamer machine is provided from said power source terminal through said power connecting terminal, moreover each of said function unit is able to be detached from said facial steamer machine by pulling out said function unit from said respective receiving chamber of said unit holding shelf and disconnecting said power source terminal and said power connecting terminal.

2. A facial steamer machine as recited in claim 1 wherein each of said power source terminals is an electrical socket serving as a power output of said facial steamer machine and each of said power connecting terminals is an electrical plug serving as a power input of said function unit, wherein each of said electrical plugs is firmly affixed to said rear side of said respective unit case and plugged into said respective electrical socket when said function unit is fully inserted into said corresponding receiving chamber of said unit holding shelf.

3. A facial steamer machine as recited claim 2 wherein a front surface of each of said electrical sockets is preferably positioned at a same plane of said respective rear wall, so that when said function units are inserted into said receiving chambers respectively, said rear sides of said unit cases of said function units are all in the proximity of said rear wall of said unit holding shelf in order to achieve better electrical connection between said electrical plugs and said electrical sockets.

4. A facial steamer machine as recited in claim 3 wherein each of said electrical plugs has two connecting tails and each of said electrical sockets has two socket holes, and that a front end of each of said socket holes is enlarged to front a guiding end to guide said insertion of said respective connecting tail of said corresponding plug.

5. A facial steamer machine as recited in claim 1 wherein said facial steamer machine is equipped with three of said function units which are preferably arranged angularly, in which said rear wall is divided into two sidewardly positioned rear walls and a middle rear wall, wherein said two sidewardly positioned rear walls are rearwardly inclined with respect to said middle rear wall, moreover two pairs of dividers are secured to a top wall and a bottom wall of said unit holding shelf respectively, and that each of said dividers comprises a tapered wedge and two of said dividers are evenly spaced and parallelly secured to said top wall while said other two dividers are evenly spaced and parallelly secured to said bottom wall so as to define three of said receiving chambers.

6. A facial steamer machine as recited in claim 3 wherein said facial steamer machine is equipped with three of said function units which are preferably arranged angularly, in which said rear wall is divided into two sidewardly positioned rear walls and a middle rear wall, wherein said two sidewardly positioned rear walls are rearwardly inclined with respect to said middle rear wall, moreover two pairs of dividers are secured to a top wall and a bottom wall of said unit holding shelf respectively, and that each of said dividers comprises a tapered wedge and two of said dividers are evenly spaced and parallelly secured to said top wall while said other two dividers are evenly spaced and parallelly secured to said bottom wall so as to define three of said receiving chambers.

7. A facial steamer machine as recited in claim 4 wherein said facial steamer machine is equipped with three of said function units which are preferably arranged angularly, in which said rear wall is divided into two sidewardly positioned rear walls and a middle rear wall, wherein said two sidewardly positioned rear walls are rearwardly inclined with respect to said middle rear wall, moreover two pairs of dividers are secured to a top wall and a bottom wall of said unit holding shelf respectively, and that each of said dividers comprises a tapered wedge and two of said dividers are evenly spaced and parallelly secured to said top wall while said other two dividers are evenly spaced and parallelly secured to said bottom wall so as to define three of said receiving chambers.

8. A facial steamer machine as recited in claim 1 further comprising a plurality of locking means for respectively securing said function units with said unit holding shelf.

9. A facial steamer machine as recited in claim 8 wherein each of said locking means includes a transverse groove provided at a bottom surface of said unit case of said respective function unit and a resilient locking member affixed underneath a bottom wall of said unit holding shelf, wherein each of said locking member has a securing rib protruded upwardly for engaging with said groove when said respective function unit is fully inserted into said corresponding receiving chamber, thereby to unlock said locking means, simply press said locking member downwards and detach said function unit by pulling out said function unit from said unit holding shelf.

10. A facial steamer machine as recited in claim 3 further comprising a plurality of locking means for respectively securing said function units with said unit holding shelf.

11. A facial steamer machine as recited in claim 10 wherein each of said locking means includes a transverse groove provided at a bottom surface of said unit case of said respective function unit and a resilient locking member affixed underneath said bottom wall of said unit holding shelf, wherein each of said locking member has a securing rib protruded upwardly for engaging with said groove when said respective function unit is fully inserted into said corresponding receiving chamber, thereby to unlock said locking means, simply press said locking member downwards and detach said function unit by pulling out said function unit from said unit holding shelf.

12. A facial steamer machine as recited in claim 4 further comprising a plurality of locking means for respectively securing said function units with said unit holding shelf.

13. A facial steamer machine as recited in claim 12 wherein each of said locking means includes a transverse groove provided at a bottom surface of said unit case of said respective function unit and a resilient locking member affixed underneath said bottom wall of said unit holding shelf, wherein each of said locking member has a securing rib protruded upwardly for engaging with said groove when said respective function unit is fully inserted into said corresponding receiving chamber, thereby to unlock said locking means, simply press said locking member downwards and detach said function unit by pulling out said function unit from said unit holding shelf.

14. A facial steamer machine as recited in claim 5 further comprising a plurality of locking means for respectively securing said function units with said unit holding shelf, wherein each of said locking means includes a transverse groove provided at a bottom surface of said unit case of said respective function unit and a resilient locking member affixed underneath said bottom wall of said unit holding shelf, wherein each of said locking member has a securing rib protruded upwardly for engaging with said groove when said respective function unit is fully inserted into said corresponding receiving chamber, thereby to unlock said locking means, simply press said locking member downwards and detach said function unit by pulling out said function unit from said unit holding shelf.

15. A facial steamer machine as recited in claim 7 further comprising a plurality of locking means for respectively securing said function units with said unit holding shelf, wherein each of said locking means includes a transverse groove provided at a bottom surface of said unit case of said respective function unit and a resilient locking member affixed underneath said bottom wall of said unit holding shelf, wherein each of said locking member has a securing rib protruded upwardly for engaging with said groove when said respective function unit is fully inserted into said corresponding receiving chamber, thereby to unlock said locking means, simply press said locking member downwards and detach said function unit by pulling out said function unit from said unit holding shelf.

16. A facial steamer as recited in claim 1 further comprising a central switch, which is electrically connected along said main power wire, is disposed on said movable stand so that said facial steamer unit and all said function units is shut off by switching off said central switch.

17. A facial steamer as recited in claim 4 further comprising a central switch, which is electrically connected along said main power wire, is disposed on said movable stand so that said facial steamer unit and all said function units is shut off by switching off said central switch.

18. A facial steamer as recited in claim 7 further comprising a central switch, which is electrically connected along said main power wire, is disposed on said movable stand so that said facial steamer unit and all said function units is shut off by switching off said central switch.

19. A facial steamer as recited in claim 15 further comprising a central switch, which is electrically connected along said main power wire, is disposed on said movable stand so that said facial steamer unit and all said function units is shut off by switching off said central switch.

20. A facial steamer as recited in claim 1 further comprising a fuse electrically connected along said main power wire to prevent unwanted and unexpected electrical shock.

21. A facial steamer as recited in claim 19 further comprising a fuse electrically connected along said main power wire to prevent unwanted and unexpected electrical shock.

22. A facial steamer machine equipped with a plurality of detachable function units each having a predetermined skin care function, wherein said facial steamer machine comprises a facial steamer unit, a system housing, and a movable stand for supporting said facial steamer unit and said system housing, said system housing comprising a central power control unit affixed to a side of said facial steamer unit and a unit holding shelf integrally mounted on said central power control unit, said unit holding shelf providing a plurality of horizontal receiving chambers adapted to receive said plurality of function units respectively, said central power control unit comprising a plurality of power source terminals, wherein each of said power source terminals is respectively mounted on a rear wall of each of said receiving chambers of said unit holding shelf and electrically connected to a main power wire of said facial steamer machine which is downwardly extended outside from a bottom portion of said movable stand, each of said function units further comprising a unit case to encase a predetermined skin care appliance therein, an operation panel provided on said unit case, and a power connecting terminal disposed on a rear side of said unit case, therefore when said function unit is firmly installed to said facial steamer machine by inserting into said respective receiving chamber of said unit holding shelf, said power connecting terminal is fittedly connected with said respective power source terminal in order to achieve electrical communication, so that an electrical power of each of said function units installed to said facial steamer machine is provided from said power source terminal through said power connecting terminal, moreover said facial steamer machine further comprises an operation unit which is affixed under said unit holding shelf and comprises a plurality of electrical connectors all electrically extended to said rear walls of said receiving chambers respectively, and that each of said function units further provides an electrical terminal at said rear side thereof for electrically connected with said respectively electrical connector when said function unit is received in said corresponding receiving chamber, wherein said operation unit provides a plurality of tool connectors thereon to connect with a plurality of operation tools via a plurality of electric wires respectively.

23. A facial steamer machine as recited in claim 22 wherein each of said power source terminals is an electrical socket serving as a power output of said facial steamer machine and each of said power connecting terminals is an electrical plug serving as a power input of said function unit, wherein each of said electrical plugs is firmly affixed to said rear side of said respective unit case and plugged into said respective electrical socket when said function unit is fully inserted into said corresponding receiving chamber of said unit holding shelf.

24. A facial steamer machine as recited claim 23 wherein a front surface of each of said electrical sockets is preferably positioned at a same plane of said respective rear wall, so that when said function units are inserted into said receiving chambers respectively, said rear sides of said unit cases of said function units are all in the proximity of said rear wall of said unit holding shelf in order to achieve better electrical connection between said electrical plugs and said electrical sockets.

25. A facial steamer as recited in claim 22 further comprising a central switch, which is electrically connected along said main power wire, is disposed on said movable stand so that said facial steamer unit and all said function units is shut off by switching off said central switch.

26. A facial steamer as recited in claim 22 further comprising a fuse electrically connected along said main power wire to prevent unwanted and unexpected electrical shock.

* * * * *